US010695538B2

United States Patent
Jaouani (10) Patent No.: US 10,695,538 B2
(45) Date of Patent: Jun. 30, 2020

(54) DEVICE FOR SECURING AN ELONGATED ELEMENT ON THE BODY OF A PATIENT, TREATMENT KIT AND ASSOCIATED METHOD

(71) Applicant: Perouse Medical, Ivry le Temple (FR)

(72) Inventor: Benjamin Lahoucine Jaouani, Creteil (FR)

(73) Assignee: PEROUSE MEDICAL, Ivry le Temple (FR)

( * ) Notice: Subject to any disclaimer, the term of this patent is extended or adjusted under 35 U.S.C. 154(b) by 0 days.

(21) Appl. No.: 14/925,840

(22) Filed: Oct. 28, 2015

(65) Prior Publication Data
US 2016/0114135 A1 Apr. 28, 2016

(30) Foreign Application Priority Data
Oct. 28, 2014 (FR) ...................................... 14 60355

(51) Int. Cl.
*A61M 25/02* (2006.01)
*A61M 25/00* (2006.01)
*A61F 13/00* (2006.01)

(52) U.S. Cl.
CPC .......... *A61M 25/02* (2013.01); *A61M 25/002* (2013.01); *A61F 2013/00412* (2013.01);
(Continued)

(58) Field of Classification Search
CPC ................. A61M 25/00; A61M 25/02; A61M 2025/0246; A61M 25/0253;
(Continued)

(56) References Cited

U.S. PATENT DOCUMENTS

| 3,826,254 A | * | 7/1974 | Mellor | A61M 25/02 128/DIG. 26 |
| 4,838,878 A | * | 6/1989 | Kalt | A61M 25/02 128/DIG. 26 |
| 5,707,348 A | * | 1/1998 | Krogh | A61M 25/02 602/41 |

(Continued)

FOREIGN PATENT DOCUMENTS

| WO | WO0211786 | 2/2002 |
| WO | 2014149668 A1 | 9/2014 |

OTHER PUBLICATIONS

Preliminary Search Report dated Jul. 24, 2015 for French Application No. FR 14 60355.

*Primary Examiner* — Nathan R Price
*Assistant Examiner* — Dung T Ulsh
(74) *Attorney, Agent, or Firm* — Davidson, Davidson & Kappel, LLC (57) ABSTRACT

An attachment device for securing an elongated element on the body of a patient is provided which includes a retaining support for retaining the elongated element, including at least one lower wall and an adhesive strip bearing the retaining support, and intended to be applied on the skin of the patient, the adhesive strip defining at least one region of the attachment device shifted with respect to the lower wall. A region of the attachment device located under the lower wall along an axis for inserting the elongated element into the retaining support is intended to be non-adherent to the skin of the patient. The retaining support comprises a clasping flap able to be maneuvered with respect to the lower wall between an open position and a clasping position of the elongated element. The elongated element is intended to be maintained between the lower wall and the clasping flap.

23 Claims, 5 Drawing Sheets

(52) U.S. Cl.
CPC ............ *A61M 2025/0246* (2013.01); *A61M 2025/0253* (2013.01); *A61M 2025/0266* (2013.01)

(58) Field of Classification Search
CPC ............ A61M 25/026; A61M 25/0266; A61M 25/028; A61M 2025/0253; A61M 2025/0266; A61F 2013/00412
See application file for complete search history.

(56) References Cited

U.S. PATENT DOCUMENTS

| | | | | |
|---|---|---|---|---|
| 5,743,885 | A * | 4/1998 | Hoerby | A61M 16/0488 128/DIG. 26 |
| 5,797,884 | A * | 8/1998 | Byrd | A61M 25/02 604/174 |
| 5,885,254 | A * | 3/1999 | Matyas | A61M 25/02 604/174 |
| 6,132,399 | A * | 10/2000 | Shultz | A61M 25/02 604/174 |
| 6,273,873 | B1 * | 8/2001 | Fleischer | A61M 25/02 604/1 |
| 6,540,724 | B1 * | 4/2003 | Harris | A61M 25/02 604/174 |
| 6,809,230 | B2 * | 10/2004 | Hancock | A61M 25/02 602/42 |
| 6,875,199 | B2 * | 4/2005 | Altman | A61F 15/008 128/846 |
| 8,251,957 | B2 * | 8/2012 | Kyvik | A61M 25/02 604/174 |
| 8,579,863 | B2 | 11/2013 | Scherr | |
| 8,636,699 | B2 | 1/2014 | Russo | |
| 2004/0143220 | A1 * | 7/2004 | Worthley | A61M 25/02 604/174 |
| 2008/0200880 | A1 * | 8/2008 | Kyvik | A61M 25/02 604/180 |
| 2014/0163515 | A1 * | 6/2014 | Hyman | A61M 25/02 604/500 |
| 2014/0194824 | A1 * | 7/2014 | Schutz | A61M 25/02 604/180 |
| 2014/0207072 | A1 * | 7/2014 | Nokes, Jr. | A61M 25/02 604/179 |
| 2014/0276604 | A1 * | 9/2014 | Maynard | A61M 25/02 604/508 |
| 2015/0119808 | A1 * | 4/2015 | Khalaj | A61M 25/02 604/180 |
| 2015/0367102 | A1 * | 12/2015 | Andino | A61M 25/02 604/179 |
| 2016/0101264 | A1 * | 4/2016 | Bertram | A61M 25/02 604/513 |
| 2016/0114135 | A1 * | 4/2016 | Jaouani | A61M 25/002 604/513 |
| 2016/0193117 | A1 * | 7/2016 | Geosits | A61M 25/02 604/516 |

* cited by examiner

DEVICE FOR SECURING AN ELONGATED ELEMENT ON THE BODY OF A PATIENT, TREATMENT KIT AND ASSOCIATED METHOD

CROSS-REFERENCE TO RELATED APPLICATIONS

This application claims the benefit of the French Application No. FR 14 60355, which was filed on Oct. 28, 2014, and which is hereby incorporated by reference in its entirety.

BACKGROUND

Field of the Invention

The present invention relates to a device for securing an elongated element on the body of a patient.

Description of the Related Art

Certain elongated elements intended to be inserted into the body of a patient give the possibility of introducing or sampling liquids in the human body, for example via the blood network.

This is notably the case of catheters, or further more especially "PICC," i.e. central catheters inserted via a peripheral route according to the English acronym.

Thus, a first end of the elongated element is introduced into the human body, while a second end is maintained outside the human body, in order to be connected to one or several supply tubes allowing passage of fluid.

The elongated element is inserted into the human body from an exit point, located on the skin of the patient, for example at an arm.

The first end of the catheter is placed in a specific injection or sampling site, for example in the vicinity of a cardiac valve. The position of the first end should be specifically maintained so as to ensure adequate distribution or sampling of the product, while avoiding the risk of complications (for example thrombosis in the case of poor placement in the blood network).

When the catheter is not used, it should be maintained in position, in order to allow the patient to move freely, without any risk of displacing the first end.

Also, when the catheter is used, the position of the first end should be maintained, in order to e.g. guarantee the effectiveness of the treatment or avoid complications.

There exist two methods for securing the second end of the elongated element. The first method consists of suturing the end of the catheter to the skin. This ensures that the attachment is effective, but is a traumatic step having risks of infection for the patient and the care-giver (in particular, risk of being pricked with the suture needle).

A second method consists of producing an attachment without any sutures, for example with a simple bandage.

Devices based on bandages have been developed for limiting the risk of mobilization of the elongated element.

Elongated elements, such as "PICCs," are generally used for long periods, and often outside the hospital for mobile patients. It is therefore necessary to regularly change the bandages which retain the second end of the elongated element to the skin of the patient. In order to reduce the risks of infection, the bandages should thus remain at most for eight days on the patient.

Removal of the existing bandage and the setting into place of a new bandage may mobilize the elongated element, which may be damageable depending on the location where the first end of the elongated element is inserted.

For example, the first end of the elongated element may be inserted into the superior vena cava. An axial displacement of the elongated element may then touch the heart or cause thrombosis. Further, a displacement of the catheter may perforate the vein in which it is found, which may generate complications and pains.

Moreover, simple reversal of the second end of the catheter, outside the patient, for setting into place the bandage or its removal may be unpleasant for the patient.

In order to overcome this problem, proposal of elongated elements including, at their second end, fins which are attached on a support with two valves, each associated with a fin, is known. The elongated element is thus maintained in every direction, and the assembly is attached on an adhesive strip. A kit of this type is described in document WO 02/11786 A2.

Such a kit does not give complete satisfaction. Indeed, upon changing the bandage, it is necessary to lift the valves retaining the elongated element, to ex-center or/and fold back the elongated element and to remove the bandage in order to disinfect the area around the exit point. This maneuver significantly mobilizes the elongated element.

Further, the aforementioned device lacks simplicity, since both hands are required for proceeding with installation and with removal of the device. Further, the grip which allows opening of the valves, on the lower edge is not clearly identified, and the grip at another location, on the upper edge or in the middle of the valve, makes it difficult to open the valve.

SUMMARY

An object of the invention is to provide a device for securing an elongated element, which further limits the risks of mobilization of the elongated element, while being simple to use both for setting it into place and for removing the device.

For this purpose, the subject-matter of the invention is a device of the aforementioned type, characterized in that at least one region of the attachment device located under the lower wall along an insertion axis for inserting the elongated element into the retaining support is intended to be non-adherent to the skin of the patient when the attachment device is secured on the skin of the patient, the retaining support comprising a clasping flap capable of being maneuvered relatively to the lower wall between an open position and a position for clasping the elongated element, wherein the elongated element is intended to be maintained between the lower wall and the clasping flap.

In some embodiments, the present invention relates to a device for securing an elongated element on the body of a patient, the device comprising:
  a retaining support for retaining the elongated element, including at least one lower wall intended to be placed between the elongated element and the body of the patient;
  an adhesive strip bearing the retaining support, and intended to be applied on the skin of the patient, the adhesive strip defining at least one shifted region of the securing device relatively to the lower wall intended to adhere to the skin of the patient,
  wherein the elongated element is intended to be partly inserted into the human body.

The device according to the invention may comprise one or several of the following features, taken individually or according to any technically possible combination:

the clasping flap is stiffer in flexure than the adhesive strip.

the retaining support comprises an attachment flap, capable of being folded back on the clasping flap in order to maintain the clasping flap in position.

the attachment flap is stiffer in flexure than the adhesive strip.

the device comprises an assembly for selectively attaching the attachment flap on the clasping flap.

the retaining support comprises at least one blocking assembly for blocking the elongated element, intended to be interposed between the lower wall and the clasping flap in the clasping position.

the blocking assembly includes at least one element in an elastically deformable material protruding from the clasping flap and/or from the lower wall.

the blocking assembly comprises a first set of pins protruding from the clasping flap and a second set of pins protruding from the lower wall.

the adhesive strip has at least one external adhesive region intended to come into contact with the body of the patient, said or each external adhesive region being shifted relatively to the retaining support and advantageously with respect to an exit point of the elongated element out of the patient.

the adhesive strip comprises at least two external adhesive regions located on either side of the retaining support with respect to the insertion axis.

the adhesive strip includes a central region located facing the retaining support, at least one external region protruding laterally with respect to the central region and with respect to the retaining support, a lower surface of the adhesive strip intended for contacting with the patient skin being totally non-adhesive in the central region, an upper surface of the adhesive strip bearing the retaining support.

the adhesive strip includes a lower surface and an upper surface, the retaining support being secured on the upper surface, advantageously by adhesive bonding.

the adhesive strip includes a lower surface and an upper surface, at least one central region of the adhesive strip being secured on an upper surface of the lower wall, the central region overlapping the lower wall.

the lower surface of the lower wall is intended to be applied on the skin of the patient being totally non-adherent with the patient.

at least one non-sliding contact element is secured on the lower surface of the lower wall.

the retaining support includes a fold-back flap, the fold-back flap being applied on the central region of the adhesive strip.

the adhesive strip comprises at least three external disconnected adhesive regions, advantageously at least four external disconnected adhesive regions, the external adhesive regions being distributed around the retaining support, on either side with respect to the insertion axis.

The subject-matter of the invention is also a treatment kit comprising a device as defined above and an elongated element intended to be partly inserted into the body of the patient, the elongated element being advantageously selected from a catheter, notably a central catheter with peripheral insertion, a central venous catheter, a dialysis catheter, a urinary catheter, a nasogastric probe, a peritoneal catheter, a Foley catheter, a draining catheter, a biliary probe, a nephrostomy probe, a gastrostomy probe, an epidural catheter, an arterial catheter, a pyelostomy tube, a perinerval catheter and/or a tubing or the body of a Huber needle.

The kit according to the invention may comprise one or several of the following features, taken individually or according to any technically possible combination:

an upper bandage intended to cover the device, the upper bandage comprising a base sheet capping the device and a maintaining flap able to be folded back on the base sheet and defining a space for immobilizing an end of the elongated element.

The subject-matter of the invention is also a method for securing an elongated element on the body of a patient, the method comprising the following steps:

providing a device as defined above;

partly inserting the elongated element into the body of the patient;

placing the clasping flap in its open position and inserting the elongated element on the lower wall by sliding the lower wall under the elongated element, without turning over the elongated element;

maneuvering the clasping flap into its clasping position;

securing at least one external region of the adhesive strip on the skin of the patient, wherein at least one region of the device located under the lower wall along an axis for inserting the elongated element into the retaining support, not adhering to the skin of the patient.

The method according to the invention may comprise one or several of the following features, taken individually or according to any technically possible combination:

detaching each external region away from the skin of the patient, by maintaining the clasping flap in its clasping position;

maneuvering the clasping flap into its open position;

extracting the device away from the patient by sliding the non-adherent region of the device located under the lower wall between the skin of the patient and the elongated element, without turning over the elongated element.

The subject-matter of the invention is also a device for securing an elongated element on the body of a patient, the elongated element being intended to be partly inserted into the body of the patient, the device including:

a support for retaining the elongated element, including at least one lower wall intended to be placed between the elongated element and the body of the patient;

an adhesive strip bearing the retaining support, and intended to be applied on the skin of the patient, the adhesive strip defining at least one shifted region of the attachment device with respect to the lower wall intended to adhere to the skin of the patient;

characterized in that the adhesive strip comprises at least three external disconnected adhesive regions, advantageously at least four external disconnected adhesive regions, the external adhesive regions being distributed around the retaining support, on either side with respect to the insertion axis, the retaining support comprising a clasping flap capable of being maneuvered with respect to the lower wall between an open position and a position for clasping the elongated element, wherein the elongated element is intended to be maintained between the lower wall and the clasping flap.

In this case, the device does not necessarily include the feature according to which at least one region of the attachment device located under the lower wall along an axis for inserting the elongated element into the retaining support is intended to be non-adherent to the skin of the patient when the attachment device is secured on the skin of the patient.

The region of the attachment device located under the lower wall may be intended to be adherent to the skin of the patient when the attachment device is secured on the skin of the patient.

In this case, the elongated element is advantageously a Huber needle.

The device according to the invention may then comprise one or several of the features listed earlier, taken alone or according to any technically possible combination.

BRIEF DESCRIPTION OF THE DRAWINGS

The invention will be better understood upon reading the description which follows, only given as an example, and made with reference to the appended drawings wherein.

DETAILED DESCRIPTION

Figure 1:
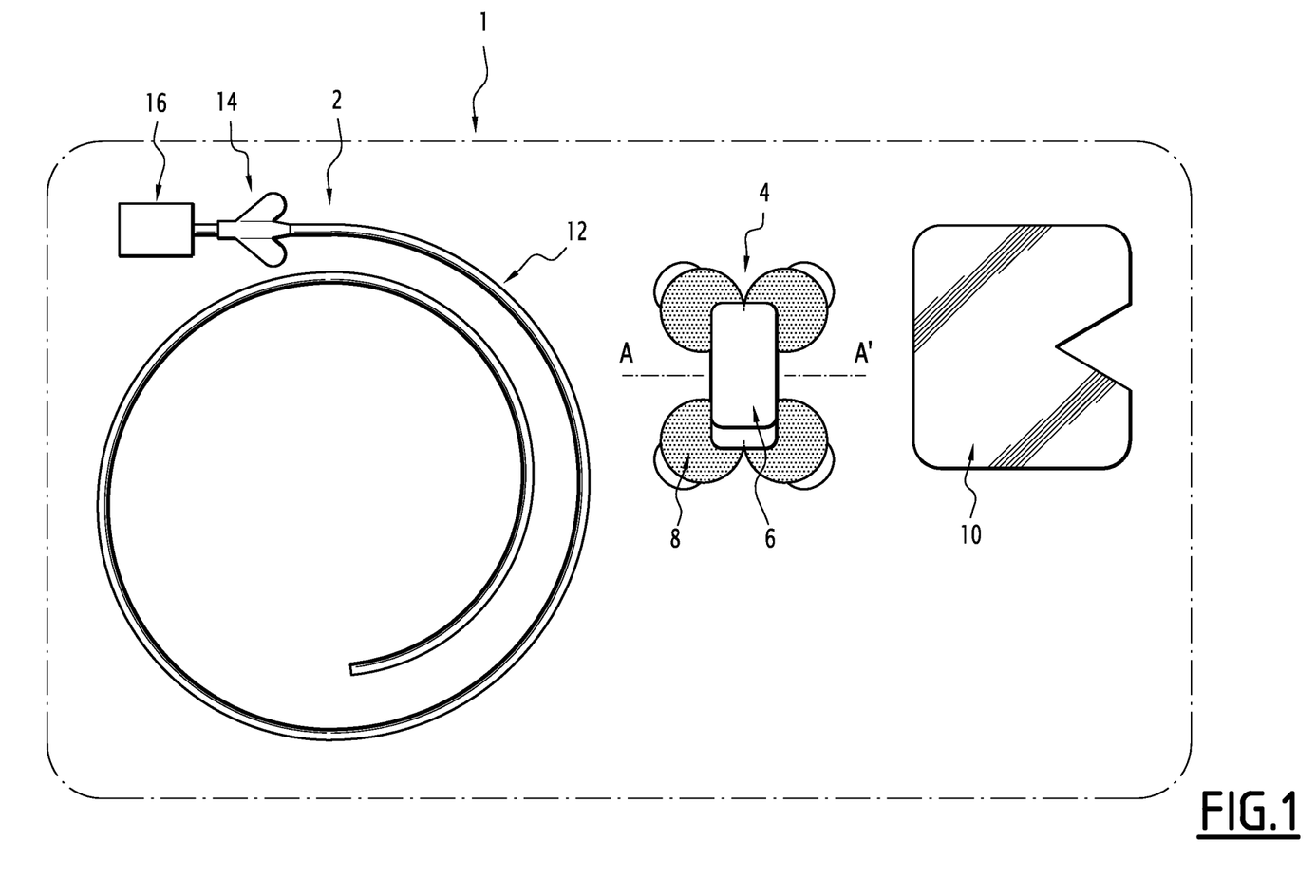
FIG. 1 is a top view of a first treatment kit according to the invention including an elongated element, a device for securing the elongated element and an upper bandage intended to cover the whole.

A first treatment kit 1 according to the invention is illustrated in FIG. 1. The kit 1 comprises an elongated element 2, intended to be at least partly introduced into the body of a patient, and a first device 4 for securing the elongated element 2 on the body of the patient.

The device 4 according to the invention comprises a retaining support 6, and an adhesive strip 8 bearing the retaining support 6 for securing it on a body surface of the patient.

The kit 1 further includes advantageously an upper bandage 10.

The elongated element 2 includes in this example a flexible tube 12, and a handling base 14.

The flexible tube 12 extends between a first end intended to be introduced into the body of the patient, for example into a vein, and a second end intended to be maintained outside the body of the patient and to be received in the retaining support 6 of the device 4.

The length of the flexible tube 12 is for example comprised between 5 cm and 60 cm, and its inner diameter is for example comprised between 0.30 mm and 8 mm.

The handling base 14 protrudes on the outside of the flexible tube 12 in the vicinity of the second end. It is permanently maintained outside the body of the patient.

The flexible tube 12 has at its second end, at least one connector 16 for fluidic connection of the elongated element 2 to at least one assembly for transferring fluid from the outside of the body of the patient towards the inside of the body of the patient (or vice versa).

Figure 2:
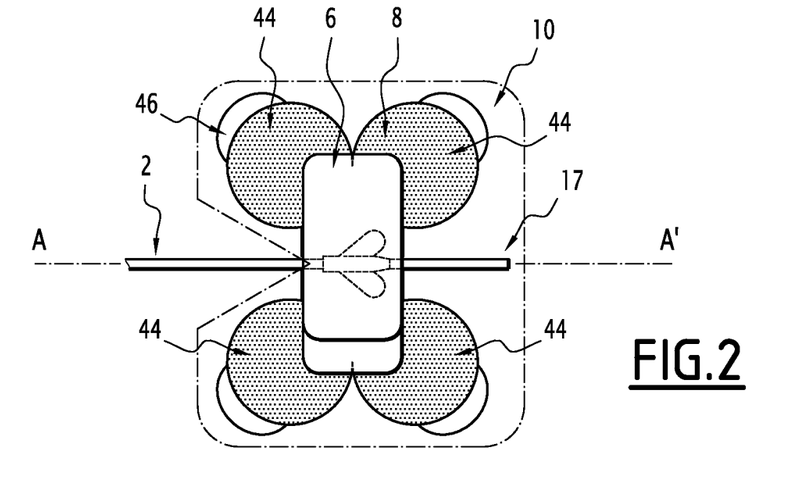
FIG. 2 is a top view of the kit after it has been set into place.

The first end of the flexible tube 12 is advantageously introduced into the body of the patient via an exit point 17 in the skin of the patient (visible in FIG. 2). It is brought as far as an injection or/and fluid-sampling site in the patient, advantageously through his/her circulatory system.

The assembly formed by the flexible tube 12 and the handling base 14 notably forms a catheter of the type of a central catheter inserted via a peripheral route or "PICC".

As indicated above, the device 4 includes the retaining support 6 secured on the adhesive strip 8.

Figure 3:
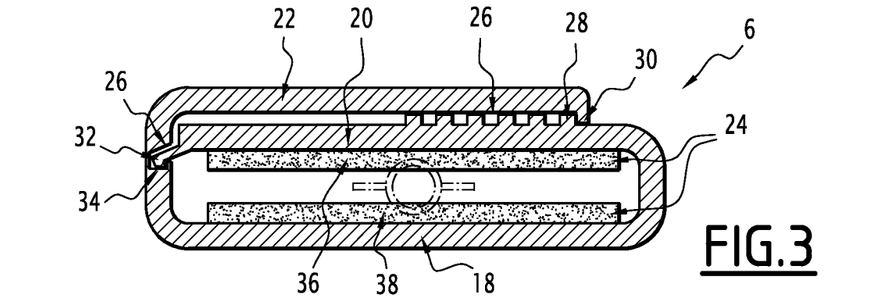
FIG. 3 is a side view of the retaining support in the attachment device of FIG. 1, including in this example a lower wall, a clasping flap and an attachment flap.

FIG. 3 illustrates a side view of the retaining support 6. The retaining support 6 is intended to reversibly maintain a portion of the elongated element 2 protruding outside the body of the patient from the exit point 17.

The retaining support 6 is formed by a clamp which comprises a lower wall 18 secured on the adhesive strip 8, a mobile clasping flap 20 with respect to the lower wall 18 between an open position and a clasping position of the elongated element 2, and advantageously an attachment flap 22, mobile with respect to the clasping flap 20 between a rest position and a position for maintaining the clasping flap 20 in the clasping position of the elongated element 2.

The retaining support 6 further includes an assembly 24 for blocking the elongated element 2, interposed between the lower wall 18 and the clasping flap 20 in the clasping position, and an adjustable attachment assembly 26 of the attachment flap 22 in its maintaining position.

The lower wall 18 of the retaining support 6 is for example of a rectangular shape. The lower wall 18 advantageously comprises one or two notches opposite to each other, comprised on the longitudinal edges of the lower wall 18, in order to allow the use of an antimicrobial and/or hemostasis bandage. This type of bandage is for example described in patent U.S. Pat. No. 8,579,863 B2.

It extends transversely relatively to an axis A-A' for introducing and maintaining the elongated element 2 in the retaining support 6.

The lower wall 18 is stiff in flexure, in the sense that it is stiffer in flexure than the adhesive strip 8.

Thus, preferably, when the side edges of the lower wall 18 are grasped between the fingers of a user, they cannot be flexed towards each other manually, or they may be flexed towards each other without being able to come into contact with each other without an irreversible deformation of the lower wall 18.

The lower wall 18 is for example made on the basis of a thermoplastic material such as PE, ABS, MABS, PU, silicone, fluoropolymer, TPE, PP or PC.

The lower wall 18 has a lower surface partly or totally secured on a central portion of the adhesive strip 8. The lower surface of the lower wall 18 is not tacky and atraumatic.

Figure 9:
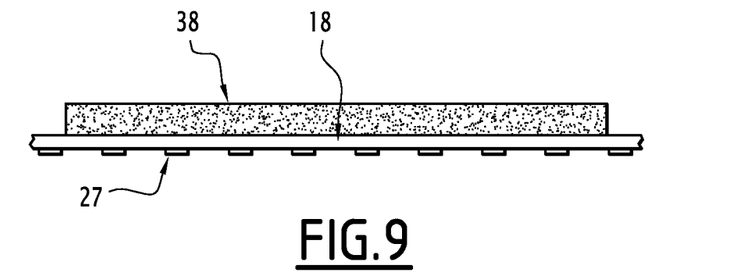
FIG. 9 is a side view of a non-sliding contact element attached against the lower wall.

As an alternative visible in FIG. 9, a non-sliding contact element 27 is attached on the lower surface of the lower wall 18. The non-sliding contact element 27 is for example foam or plate made in silicone, PU or TPE. In the example illustrated in FIG. 9, the non-sliding contact element 27 includes several small strips positioned parallel with each other, perpendicularly to the axis A-A'. The small strips define between them channels allowing circulation of air, which improves breathing of the skin when the device 4 is installed on the skin of the patient.

Advantageously, the small strips are in foam.

As this will be seen below, according to the invention, the retaining support 6 is non-adherent to the skin of the patient facing at least one region of the lower wall 18, located in the axis A-A', advantageously facing the lower wall 18.

The clasping flap 20 is also stiff in flexure, as defined earlier. It has a length substantially equal to that of the lower wall 18, as visible in FIG. 4.

Figure 4:
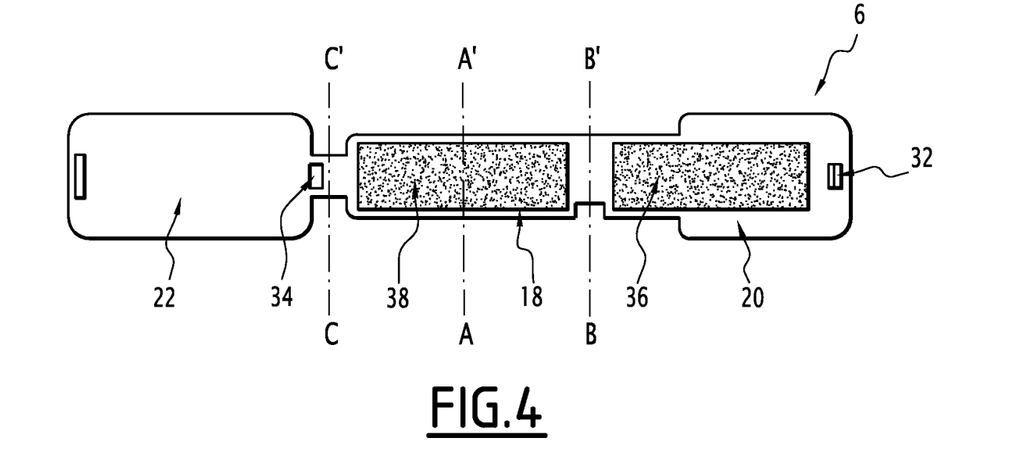
FIG. 4 is a top view of the retaining support of FIG. 3 when it occupies its unfolded position.

The clasping flap 20 is jointed on a first side edge of the lower wall 18, around a joint axis B-B' substantially parallel to the introduction and maintaining axis A-A'.

It is capable of being folded back on the lower wall 18, by pivoting around the axis B-B' between the open position, visible in FIG. 4, and the clasping position of the elongated element 2, visible in FIG. 3.

In the open position, the clasping flap 20 is shifted sideways relatively to the lower wall 18. The elongated element 2 is able to be introduced without any pivoting around the exit point 17, by inserting the lower wall 18 under the elongated element 2 following a transverse movement relatively to the axis A-A', or following an axial movement relatively to the axis A-A'.

In the clasping position, the clasping flap 20 has pivoted around the axis B-B', so as to placed facing the lower wall 18, above the latter. The elongated element 2 is able to be blocked between the clasping flap 20 and the lower wall 18 in this position.

The attachment flap 22 is jointed on the lower wall 18 along a second side edge of the lower wall 18 around a pivot axis C-C' parallel to the axis A-A' and to the axis B-B', and opposite to the first edge.

It has a length substantially identical with that of the clasping flap 20 and with that of the lower wall 18.

It is able to be folded back onto the clasping flap in its clasping position, by pivoting around the axis C-C' between the open position, visible in FIG. 4, and the position for maintaining the clasping flap, visible in FIG. 3.

Figure 5:
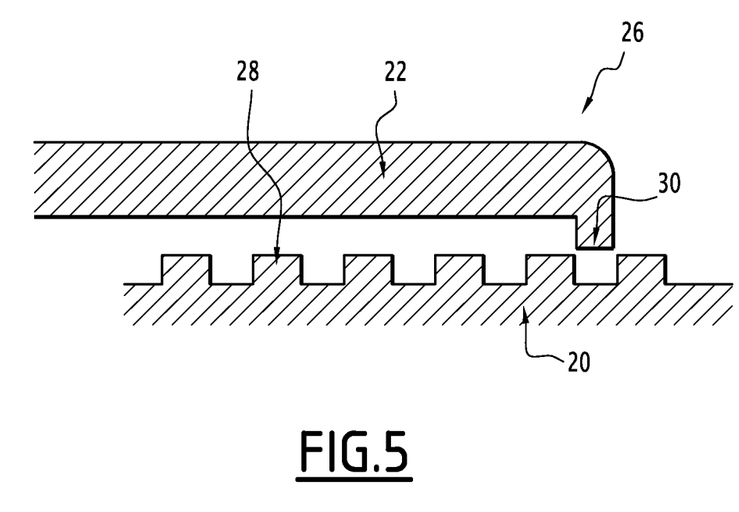
FIG. 5 is a side view of the mechanism for selectively securing the attachment flap on the clasping flap of the retaining support of FIG. 3.

As illustrated in FIG. 5, an end region of the attachment flap 22 is able to be selectively secured in length on the clasping flap 20 via the attachment assembly 26.

The attachment flap 22 is also stiff in flexure, as defined earlier.

With reference to FIG. 5, the attachment assembly 26 for example includes recesses 28 formed in an upper surface of the clasping flap 20, and a hooking-up protrusion 30 formed in a lower surface of the attachment flap 22.

The recesses 28 are spaced out transversely with respect to the axis A-A', along the clasping flap 20. They define a plurality of areas for hooking up the hooking-up protrusion 30, transversely spaced out with respect to the axis A-A'.

The selective attachment of the hooking-up protrusion 30 in one of the recesses 28 adapts the clasping of the elongated element 2 according to its size or its shape, and forms with the clasping flap 20, additional uphold of the elongated element 2.

Advantageously, the attachment assembly 26 further includes a reversible attachment element 32 of the clasping flap on the lower wall, and an element 34 for receiving the reversible attachment element 32.

The reversible attachment element 32 is for example formed by a hook protruding transversely to the free end of the clasping flap 20. The receiving element 34 is formed with a housing for receiving the hook, made in the lower wall 18 in the vicinity of the axis C-C'.

In a first alternative, the attachment assembly 26 comprises a first strip in Velcro (not shown) and a second strip in Velcro (not shown). The first Velcro strip is attached on an upper surface of the clasping flap 20. The second Velcro strip is attached on a lower surface of the attachment flap 22.

In an alternative, a strip and hook Velcro combination forms the attachment assembly.

Figure 10:
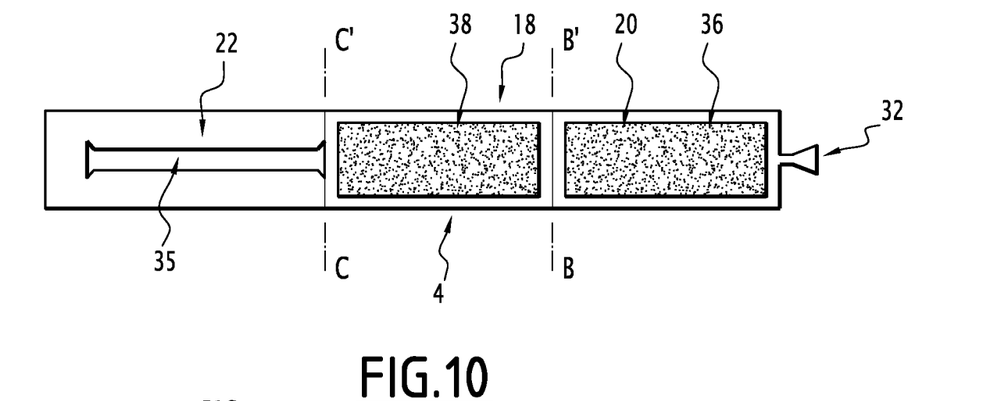
FIG. 10 is a top view of the retaining support in the unfolded position, in the presence of a second selective attachment mechanism according to the invention.

In a second alternative illustrated in FIG. 10, the attachment assembly 26 comprises a groove 35 crossing the attachment flap 22, into which the reversible attachment element 32 may engage.

The groove 35 extends along a longitudinal axis of the attachment flap 22, here perpendicularly to the axis A-A'.

The width of the groove 35 is greater than the width of the reversible attachment element 32.

According to an embodiment, the width of the groove 35 is constant over the whole length of the groove 35.

According to another embodiment, the width of the groove 35 decreases when it approaches the axis C-C'.

In the open position, the reversible attachment element 32 is able to be introduced into the groove 35 at one end of the groove. It is able to slide towards an opposite end of the groove upon passing into the clasping position.

The blocking assembly 24 is intended, when the clasping flap 20 occupies its clasping position, to maintain in place the elongated element 2 between the lower wall 18 and the clasping flap 20.

Figure 7:
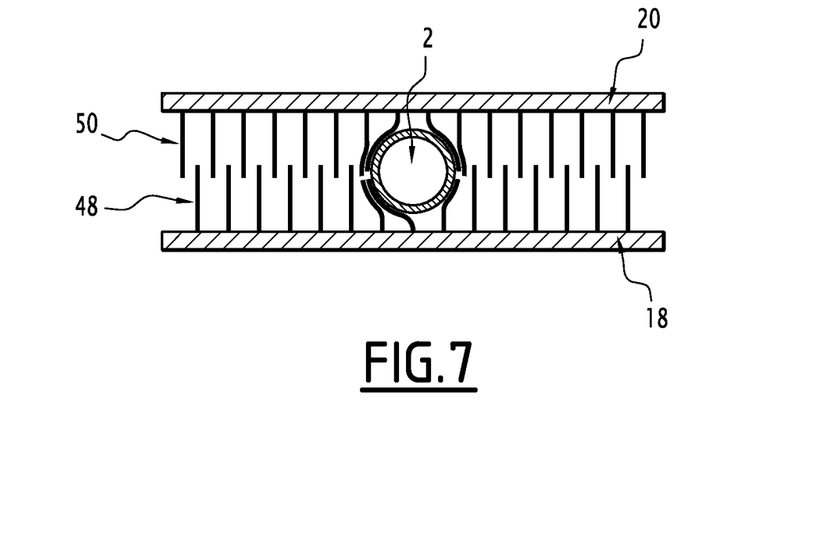
FIG. 7 is a side view of an alternative system for hooking up the elongated element for an attachment device including pins.

The blocking assembly 24 for example includes elements in an elastically deformable material, for example foam blocks, as illustrated in FIG. 3, or pins, as illustrated by FIG. 7.

Alternatively, the blocking assembly 24 is advantageously made on the basis of relatively hard thick foam, less hard than the clasping flap 20, and includes a universal cutout allowing any handling base 14 to be placed. The blocking assembly 24 reinforces the maintaining of the elongated element 2 by its height and by the shape of the cutout.

In the example illustrated by FIG. 3 and by FIG. 4, the blocking assembly 24 includes at least one first element in a deformable material 36 borne by an upper surface of the lower wall 18, and at least one second element in a deformable material 38, borne by a lower surface of the clasping flap 20.

The adhesive strip 8 is intended to secure the retaining support 6 on the skin of the patient. It defines a lower surface 40 intended to come into contact with the skin of the patient and an upper surface 42, bearing the retaining support 6. In this example, the support 6 is secured on the upper surface.

In the example illustrated in FIG. 2, the adhesive strip 8 includes a central region located facing the retaining support 6 and at least one external region 44 protruding laterally with respect to the central region and with respect to the retaining support 6.

In the central region, the lower surface 40 is at least partly non-adhesive, and preferably totally non-adhesive. Thus, upon withdrawing the attachment device 4, the central region bearing the retaining support 6 is able to be withdrawn by sliding on the skin, without having to significantly lift the elongated element 2, and in any case without having to turn it over. Further, there is no risk of detachment of the bandage 8 with respect to the retaining support 6 in the case of sweating or oozing.

Preferably, the adhesive strip 8 includes at least two external opposite regions 44, located on either side of the axis A-A', while delimiting between them along the axis A-A', the central region.

Advantageously, in the example illustrated in FIG. 1, the adhesive strip 8 has a shape of a four-leaf clover, with four external regions 44 angularly distributed around the central region, while forming disconnected petals.

Two external regions 44 are located on one side of the axis A-A', and two other external regions 44 are located on another side of the axis A-A'.

The external regions 44 located on either side of the axis A-A' delimit between them an intermediate space extending along the central axis A-A' without any external region 44.

Each external region 44 is located away from the retaining support 6 and is therefore accessible to the user, without having to lift the retaining support 6, notably for detaching them from the skin of the patient.

In each external region 44, the lower surface 40 is at least partly adhesive, preferably is totally adhesive. It is advantageously provided with a removable protective tab 46 attached below the adhesive portion of the lower surface 40. Preferably, the protective tab 46 partly protrudes outwards relatively to the adhesive strip 8, in order to allow easy withdrawal of the protective tab 46, in order to expose the adhesive portion of the lower surface 40.

The upper surface 42 bears the retaining support 6. The central region of the upper surface 42 retains the retaining support 6 by an adhesive, the other portions of the upper surface 42 being without any adhesive.

The adhesive strip 8 is deformable. It is less rigid in flexure than the lower wall 18.

Thus, preferably, when the side edges of the adhesive strip 8 are grasped between the fingers of a user, they may be bent towards each other manually, until they come into contact with each other, reversibly.

The upper bandage 10 is used for maintaining the assembly formed by the device 4 retaining the elongated element 2, on the skin of the patient. It is an additional means for securing the elongated element 2.

The upper bandage 10 is for example of a rectangular shape (FIGS. 1 and 2), with a V-shaped notch at the middle of one of its sides, so as to better maintain the assembly formed by the elongated element 2, the retaining support 6 and the adhesive strip 8.

The V-shaped notch on the upper bandage 10 is located along the axis A-A' on the side opposite to the exit point 17. Thus, it is possible to view the exit point 17, even when the device 4 is installed on the skin of the patient.

Figure 11:
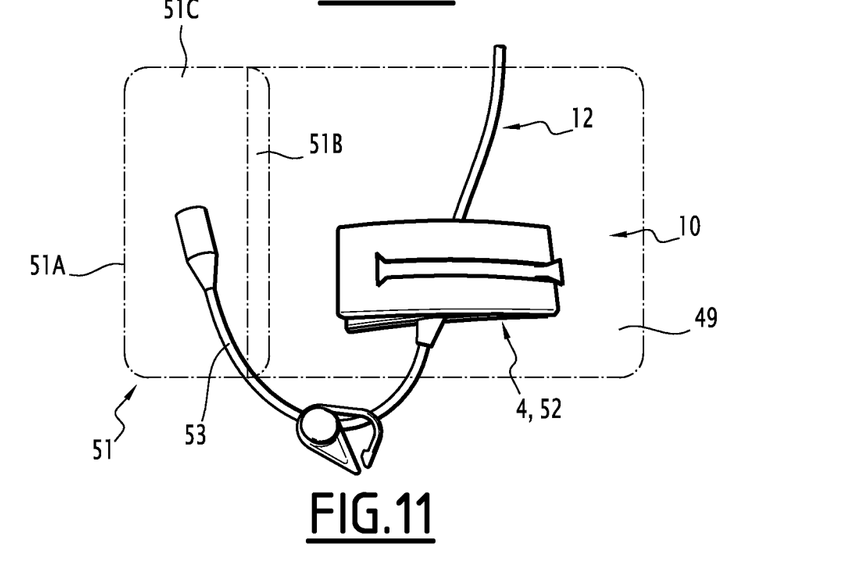
FIG. 11 is a top view of the kit after it has been set into place, wherein the upper bandage comprises a flap for maintaining an end of the elongated element.

In an alternative illustrated in FIG. 11, the upper bandage 10 includes a base sheet 49, intended to cap the device 4 and a flap 51 for maintaining the end 53 of the elongated element 2, jointed on the base sheet 49 with a first edge 51A.

The internal surface of the base sheet 49 is at least partly adhesive so as to adhere onto the skin of the patient. The external surface of the base sheet is advantageously non-adhesive.

The maintaining flap 51 is able to be folded back onto the upper bandage 10.

The upper surface of the maintaining flap 51 is non-adhesive. The lower surface of the maintaining flap 51 is non-adhesive in a central area 51C of the maintaining flap 51. It is adhesive along the first edge 51A and along a second edge 51B of the maintaining flap 51.

The internal surface of the maintaining flap 51 and the external surface of the sheet 49 define between them an intermediate space for immobilizing the end 53 of the elongated element 2.

Thus, regardless of the length of the flexible tube 12, it is possible to bring the end 53 of the flexible tube 12 to bear upon the external surface of the sheet 49, after setting into place the sheet 49 on the device 4, while leaving the maintaining flap open. The end 53 is then attached onto the outer surface by folding back the maintaining flap 51.

The operation of the attachment kit 1 will now be described.

Initially, the elongated element 2 has been set into place in the body of the patient. It has a first end located at an injection site, an internal segment extending in the patient as far as the exit point 17, and an external segment protruding out of the body of the patient, on the skin of the patient, as far as a second end along an axis A-A'.

An attachment kit 1 is then provided. The operator grasps the device 4 and places the clasping flap 20 in its open position, and the attachment flap 22 in its rest position.

The operator then orients the retaining support 6 along an axis perpendicular to the axis A-A' of the elongated element 2. The clasping flap 20 is in its open position. The retaining support 6 may be placed optionally in one direction or in the other along the axis perpendicular to the axis A-A'.

The operator then slides the adhesive strip 8 provided with protective tabs 46 and the lower wall 18 under the elongated element 2, either laterally or axially while maintaining the elongated element 2 in position.

The lifting of the elongated element 2 is minimum, which limits its mobilization. In no way is it necessary to turn the elongated element 2 over around the exit point 17. As the central region is without any adhesive, the support easily slides on the skin under the elongated element.

The clasping flap 20 is then pivoted around the axis B-B' in order to have it pass into its clasping position, and transversely grasp the elongated element 2, in the blocking assembly 24.

The reversible attachment element 32 located at the end of the clasping flap 20 is introduced into the receiving element 34 made in the lower wall 18.

Next, the attachment flap 22 is pivoted around the axis C-C' so as to be folded back onto the clasping flap 20. Depending on the height of the elongated element 2 clasped between the clasping flap 20 and the lower wall 18, the operator introduces the hooking-up protrusion 30 in a suitable recess 28.

The elongated element 2 is then maintained in position in the retaining support 6.

The protective tabs 46 of the external regions 44 of the adhesive strip 8 are then removed. The adhesive strip 8 is firmly secured onto the skin of the patient.

Next, the upper bandage 10 is placed on the device 4 for protecting it.

Upon withdrawal of the device, the upper bandage 10 is removed first.

The external regions 44 of the adhesive strip 8 are then detached. The external regions 44 are then advantageously again adhesively bonded on themselves in order to avoid that they again adhere on the skin. The attachment flap 22 and the clasping flap 20 have respectively passed again into their rest position and into their open position.

According to the invention, as the central region of the adhesive strip 8 located facing the retaining support 6 is non-adherent with the skin of the patient, the device 4 may again be slid under the elongated element 2 and the skin of the patient, without having to lift the elongated element 2.

Unlike the devices known from the state of the art, the setting into place and the withdrawal of the device 4 do not require significant lifting of the elongated element 2, by the use of a retaining support 6 formed with a clamp, and by the non-adherence of the device 4 on the skin of the patient facing the retaining support 6.

Thus, the device 4 may be set into place and withdrawn with minimum mobilization of the elongated element 2.

During the withdrawal of the attachment device 4, one hand of the user maintains the elongated element 2 and the other hand handles the attachment device 4.

When the withdrawal of the attachment device 4 is carried out for installing a new attachment device 4, it is not necessary to clean with alcohol the portion of the elongated element 2 maintained previously by the attachment device 4, since no portion of the attachment device 4 retaining the elongated element 2 is tacky. Further, the attachment device 4 is able to be used equally in an axial direction or in the other, which facilitates the work of the practitioner.

In one alternative, the blocking assembly 24 of the elongated element 2 includes two sets of opposite pins as illustrated in FIG. 7. A first set of pins 48 protrudes upwards from the upper surface of the lower wall 18, and a second set of pins 50 protrudes downwards from the lower surface of the clasping flap 20 so as to be inserted between the pins of the first set of pins 48 in the clasping position.

Such a blocking assembly 24 has the advantage of maintaining and of being adapted to any type of elongated element 2, regardless of its shape or its diameter.

Figure 6:
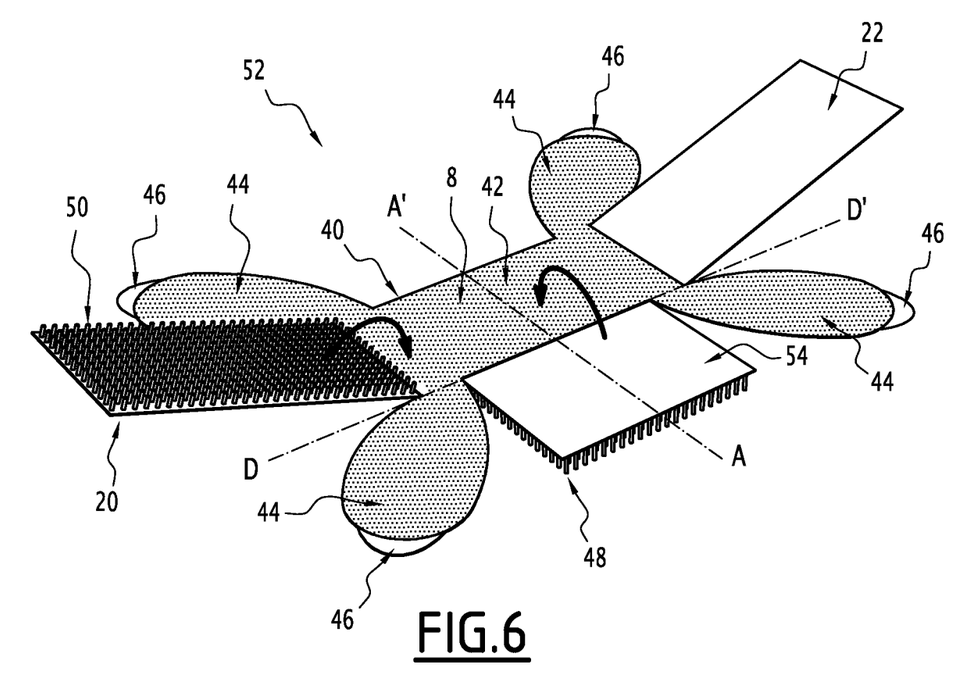
FIG. 6 is a perspective view of a second attachment device according to the invention during its mounting.

FIG. 6 schematically illustrates a second attachment device 52 according to the invention.

Unlike the first device 4, the adhesive strip 8 is in contact with the skin of the patient at external regions 44, but not at its central region.

The central region of the adhesive strip 8 overlaps the lower wall 18, so as to be attached on the latter. The upper surface of the lower wall 18 is applied upon the lower surface 40 of the adhesive strip 8, at the central region.

The lower surface of the lower wall 18 is applied against the skin of the patient. This lower surface is without any adhesive and is non-adherent with the skin of the patient. As described earlier, a non-sliding contact element 27 is advantageously attached on the lower surface of the lower wall 18.

Advantageously, the retaining support 6 has, in addition to the lower wall 18, the clasping flap 20 and the attachment flap 22, a folding-back flap 54 on the central region of the adhesive strip 8.

The folding-back flap 54 has a smaller length than that of the lower wall 18. It is jointed on the lower wall 18, along a longitudinal edge around an axis D-D' substantially perpendicular to the axis A-A'.

During the mounting of the device 6, the folding-back flap 54 is able to be folded back on the central portion of the adhesive strip 8 at the lower wall 18, between an open position and a folded-back position, in which it covers the central region of the adhesive strip 8.

Advantageously, as illustrated by FIG. 6, the folding-back flap 54 has on its upper face a first set of pins 48.

The clasping flap 20 has on its lower face a second set of pins 50, so that, upon folding back onto the clasping flap 20, both sets of pins defined earlier are inserted into each other.

When the folding-back flap 54 and the clasping flap 20 are in a folded-back position, the elongated element 2 is thus maintained between both sets of pins 48 and 50.

Upon mounting the device 6, the central region of the adhesive strip 8 is attached on the retaining support 6.

The folding-back flap 54 is maintained in its open position. The adhesive strip 8 is brought so as to face the lower wall 18. The upper surface of the lower wall 18 of the retaining support 6 is then secured by adhesive bonding to the central region of the lower surface 40 of the adhesive strip 8.

And then, the folding-back flap 54 is placed in a folded-back position, by pivoting around the axis D-D' with a first set of pins 48 on its upper surface.

During the use of the device 6, the elongated element 2 is then positioned on the folding-back flap 30, and is then maintained by the clasping flap 20 in the clasping position, as described earlier.

Advantageously, the lower wall 18, the clasping flap 20, the attachment flap, the folding-back flap and the two sets of pins are formed in one piece made in the same material, for example based on a thermoplastic material such as PE, ABS, MABS, PU, silicone, a fluoropolymer, TPE, PP, or PC.

The second device according to the invention 6 is therefore particularly simple and inexpensive to make.

Figure 8:
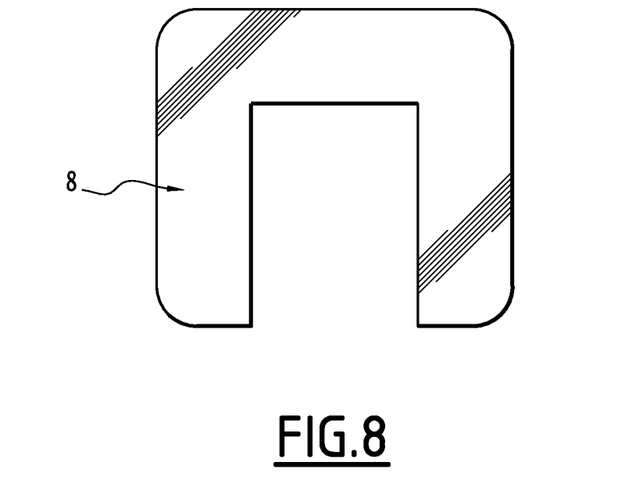
FIG. 8 is a schematic illustration of the adhesive strip according to a second embodiment.

In an alternative, illustrated by FIG. 8, the adhesive strip 8 has a U-shape. It thus has parallel branches forming external adhesive regions connected together by a central branch.

The retaining support 6 is attached to each of its ends on the parallel branches of the U.

The lower surface of the retaining support 6 is positioned between the parallel branches of the adhesive strip 8 and is non-adherent to the skin of the patient.

In another alternative, the treatment kit 1 does not comprise any elongated element 2. In this case, the elongated element 2 is provided separately.

By means of the invention which has just been described, it is possible to view the exit point 17 of the elongated element 2, even in the case of an overlap with an opaque upper bandage 10.

The attachment device 4, 52 may be used regardless of the externalized length of the elongated element 2.

The mobilization of the elongated element 2 is minimum during the laying and the withdrawal, and the device 4, 52 is neither invasive nor traumatic, in particular by the presence of a lower wall 18 at least partly non-adhesive.

In an alternative of the device of FIG. 2, the region of the attachment device 4 located under the lower wall 18 is intended to be adherent to the skin of the patient when the attachment device 4 is secured on the skin of the patient.

In this case, the elongated element 2 is advantageously a Huber needle.

It results directly and unambiguously from the above description that the elongated element 2 is retained between the clasping flap 20 and the lower wall 18 in the clasping position, exclusively by mechanical cooperation. No adhesive is put in contact with of the elongated element 2 neither between the elongated element 2 and the clasping flap 20, nor between the elongated 2 and the lower wall 18. When the clasping flap 20 occupies its open position, the retaining support 6 is fully movable with regard to the elongated element 2, without having to unstick the elongated element 2 from the retaining support 6.

What is claimed is:

1. An attachment device for securing an elongated element on a body of a patient, the attachment device comprising:

a retaining support for retaining the elongated element, comprising a lower wall intended to be placed between the elongated element and the body of the patient;

an adhesive strip bearing the retaining support, wherein the adhesive strip is configured for being applied on the skin of the patient, the adhesive strip defining a central region and at least two shifted regions of the attachment device that are shifted with respect to the lower wall, wherein the adhesive strip is configured for being adhered to the skin of the patient in each shifted region and for being non-adhesive in the central region;

at least one region of the attachment device located under the lower wall along an insertion axis for inserting the elongated element into the retaining support configured for being non-adherent to the skin of the patient when the attachment device is secured onto the skin of the patient, wherein the retaining support comprises a clasping flap configured for being maneuvered with respect to the lower wall between an open position and a clasping position of the elongated element, in which the elongated element is maintainable between the lower wall and the clasping flap, wherein the elongated element is configured for being partly inserted into the body of the patient, wherein an entire region of the attachment device located under the retaining support is configured for being non-adherent to the skin of the patient, wherein the central region is secured to the retaining support, the central region being continuous and continuously connecting to all the shifted regions, wherein the clasping flap is stiffer in flexure than the adhesive strip.

2. The attachment device according to claim 1, wherein the clasping flap is stiffer in flexure than the adhesive strip.

3. The attachment device according to claim 1, wherein the retaining support comprises an attachment flap, able to be folded back onto the clasping flap in order to maintain the clasping flap in position.

4. The attachment device according to claim 3, wherein the attachment flap is stiffer in flexure than the adhesive strip.

5. The attachment device according to claim 3, comprising an assembly for selectively attaching the attachment flap on the clasping flap.

6. The attachment device according to claim 1, wherein the retaining support comprises at least one blocking assembly for blocking the elongated element, wherein the blocking assembly is configured for being interposed between the lower wall and the clasping flap in the clasping position.

7. The attachment device according to claim 6, wherein the blocking assembly comprises at least one element made of an elastically deformable material protruding from the clasping flap, from the lower wall, or from both.

8. The attachment device according to claim 6, wherein the blocking assembly comprises a first set of pins protruding from the clasping flap and a second set of pins protruding from the lower wall.

9. The attachment device according to claim 1, wherein the adhesive strip has at least one external adhesive region configured to come into contact with the body of the patient, the at least one external adhesive region being shifted with respect to the retaining support.

10. The attachment device according to claim 9, wherein the at least one external adhesive region is shifted with respect to an exit point of the elongated element out of the body of the patient.

11. The attachment device according to claim 1, wherein the at least two regions are located on either side of the retaining support with respect to the insertion axis.

12. The attachment device according to claim 1, wherein the adhesive strip includes a lower surface and an upper surface, the retaining support being secured on the upper surface.

13. The attachment device according to claim 12, wherein the retaining support is secured on the upper surface by adhesive bonding.

14. The attachment device according to claim 1, wherein the adhesive strip includes a lower surface and an upper surface, wherein the central region of the adhesive strip is secured on an upper surface of the lower wall, the central region overlapping the lower wall.

15. The attachment device according to claim 14, wherein at least one non-sliding contact element is secured on the lower surface of the lower wall.

16. The attachment device according to claim 1, wherein the retaining support includes a folding-back flap, the folding-back flap being applied on the central region of the adhesive strip.

17. A treatment kit comprising the attachment device according to claim 1 and an elongated element configured for being partly inserted into the body of the patient.

18. The treatment kit according to claim 17, wherein the elongated element is one of a catheter, a central catheter with peripheral insertion, a central venous catheter, a dialysis catheter, a urinary catheter, a nasogastric probe, a peritoneal catheter, a Foley catheter, a draining catheter, a biliary probe, a nephrostomy probe, a gastrostomy probe, an epidural catheter, an arterial catheter, a urinary drainage probe, a perinerval catheter or a tube or the body of a Huber needle.

19. The treatment kit according to claim 17, comprising an upper bandage configured to cover the attachment device, the upper bandage comprising a base sheet capping the attachment device and a maintaining flap able to be folded back onto the base sheet and defining a space for immobilizing one end of the elongated element.

20. A method for securing an elongated element on the body of a patient, the method comprising the steps of:
providing the attachment device according to claim 1;
partly inserting the elongated element into the body of the patient;
placing the clasping flap in its open position and inserting the elongated element on the lower wall by sliding the lower wall under the elongated element, without turning the elongated element over;
maneuvering the clasping flap into the clasping position; and
securing at least one of the at least two shifted regions of the adhesive strip on the skin of the patient, wherein the at least one region of the attachment device located under the lower wall along the insertion axis for inserting the elongated element in the retaining support is non-adherent to the skin of the patient.

21. The method according to claim 19, comprising the steps of:
detaching each of the at least two shifted regions away from the skin of the patient, while maintaining the clasping flap in its clasping position;
maneuvering the clasping flap from the clasping position into the open position;
extracting the attachment device away from the patient by sliding the non-adherent region of the attachment device located under the lower wall between the skin of the patient and the elongated element, without turning over the elongated element.

22. The attachment device according to claim 1, wherein the attachment device is configured for being extracted away from the patient, after detaching each of the at least two shifted regions away from the skin of the patient, by sliding the non-adherent region of the attachment device located under the lower wall between the skin of the patient and the elongated element, without turning over the elongated element.

23. An attachment device for securing an elongated element on a body of a patient, the attachment device comprising:
- a retaining support for retaining the elongated element, comprising a lower wall intended to be placed between the elongated element and the body of the patient;
- an adhesive strip bearing the retaining support, the adhesive strip being configured for being applied on the skin of the patient,
- wherein the elongated element is configured for being partly inserted into the body of the patient,
- wherein the retaining support comprises a clasping flap configured for being maneuvered with respect to the lower wall between an open position and a clasping position of the elongated element, in which the elongated element is maintainable between the lower wall and the clasping flap,
- wherein an entire region of the attachment device located under the retaining support is configured for being non-adherent to the skin of the patient when the attachment device is secured onto the skin of the patient,
- wherein the adhesive strip comprises a central region and at least three external disconnected adhesive regions, the adhesive strip being non-adhesive in the central region, the at least three external disconnected adhesive regions being shifted with respect to the lower wall and extending laterally from the region located under the retaining support, the adhesive strip being configured for being adhered to the skin of the patient in each of the at least three external disconnected adhesive regions,
- wherein the central region is secured to the retaining, the central region being continuous and continuously connecting to all the adhesive regions,
- wherein the clasping flap is stiffer in flexure than the adhesive strip.

* * * * *